US00PP32468P3

(12) United States Plant Patent
Trigiano et al.

(10) Patent No.: US PP32,468 P3
(45) Date of Patent: Nov. 17, 2020

(54) ***CORNUS FLORIDA* TREE NAMED 'ERICA'S APPALACHIAN SUNRISE'**

(50) Latin Name: ***Cornus florida* L.**
Varietal Denomination: Erica'3 s Appalachian Sunrise

(71) Applicant: UNIVERSITY OF TENNESSEE RESEARCH FOUNDATION, Knoxville, TN (US)

(72) Inventors: Robert N. Trigiano, Knoxville, TN (US); Phillip A. Wadl, Charleston, SC (US)

(73) Assignee: UNIVERSITY OF TENNESSEE RESEARCH FOUNDATION, Knoxville, TN (US)

( * ) Notice: Subject to any disclaimer, the term of this patent is extended or adjusted under 35 U.S.C. 154(b) by 0 days.

(21) Appl. No.: 16/602,052

(22) Filed: Jul. 26, 2019

(65) Prior Publication Data

US 2020/0323117 P1 Oct. 8, 2020

Related U.S. Application Data

(60) Provisional application No. 62/830,694, filed on Apr. 8, 2019.

(51) Int. Cl.
*A01H 5/00* (2018.01)
*A01H 6/00* (2018.01)

(52) U.S. Cl.
USPC ..... Plt./220
CPC ..... *A01H 6/00* (2018.05)

(58) Field of Classification Search
USPC ..... Plt./220
CPC ..... A01H 5/02; A01H 5/00
See application file for complete search history.

(56) References Cited

PUBLICATIONS

Wadl, P.A. et al. "Molecular Identification Keys for Cultivars and Lines of *Cornus florida* and *C. kousa* Based on Simple Sequence Repeat Loci" *Journal of the American Society for Horticultural Science,* 2008, pp. 783-793, vol. 133, No. 6.

*Primary Examiner* — Kent L Bell
(74) *Attorney, Agent, or Firm* — Saliwanchik, Lloyd & Eisenschenk

(57) ABSTRACT

A new and distinct cultivar of flowering dogwood tree, which produces both fully dark red bracts and lighter red to pink bracts is provided. This dogwood tree is botanically known as *Cornus florida* and referred to by the following cultivar name: 'Erica's Appalachian Sunrise'.

3 Drawing Sheets

Specification includes a Sequence Listing.

This invention was made with Government support under Contract No. NACA-58-6062-6 awarded by the U.S. Department of Agriculture. The Government has certain rights in the invention.

The Sequence Listing for this application is labeled "Seq-List.txt" which was created on Oct. 29, 2019 and is 4 KB. The entire content of the sequence listing is incorporated herein by reference in its entirety.

BACKGROUND OF THE INVENTION

The present invention relates to a new and distinct cultivar of flowering dogwood tree with a mixture of both fully dark red and lighter red bracts. This new cultivar was the result of a controlled cross that produced a few seeds, which were planted in a greenhouse in Knoxville, Tenn. This new cultivar was discovered among the resulting seedlings. This dogwood tree is botanically known as *Cornus florida* L. and is hereinafter referred to by the following cultivar name: 'Erica's Appalachian Sunrise'. Analysis has shown that this new dogwood cultivar is the result of self-pollination of the dogwood cultivar 'Cherokee Brave' (U.S. Plant Pat. No. 10,166). The seedling of 'Erica's Appalachian Sunrise' was harvested on its own rootstock. Results have shown that the unique features of this new dogwood cultivar are stable and reproduced true-to-type in successive vegetative generations.

DETAILED DESCRIPTION OF THE NEW VARIETY

Figure 1:
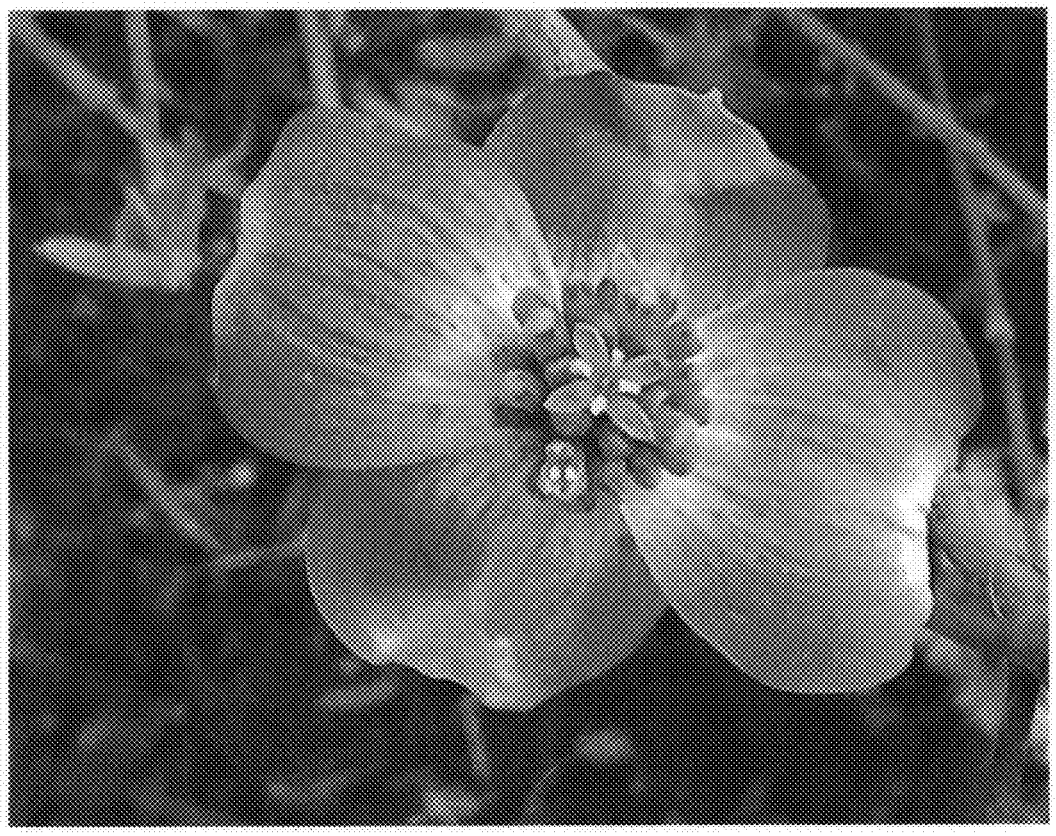
FIG. 1. Photograph of one type of bracts and flowers of the dogwood cultivar 'Erica's Appalachian Sunrise'. This bract has fully dark red coloration and is less than about 5% of the bracts produced by the cultivar. Colors in the photograph may differ from actual colors due to lighting and light reflectance.
Figure 2:
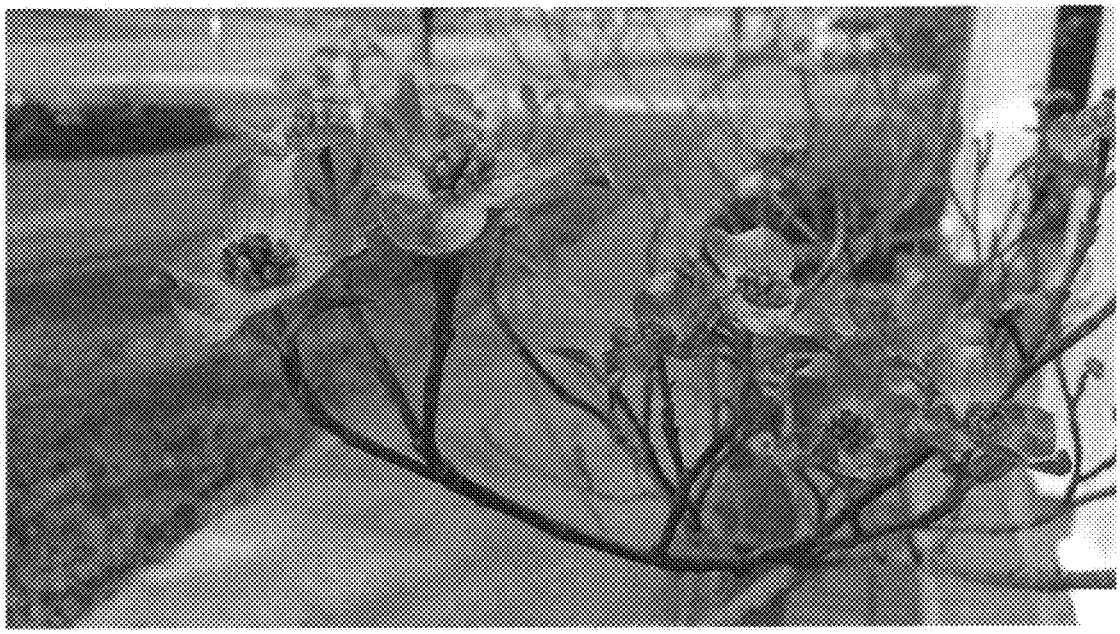
FIG. 2. Photograph of 'Erica's Appalachian Sunrise' dogwood cultivar showing the other type of bract and flowers produced more than about 95% of the time on the dogwood tree, which has lighter red or more pink bracts. Colors in the photograph may differ from actual colors due to lighting and light reflectance.
Figure 3:
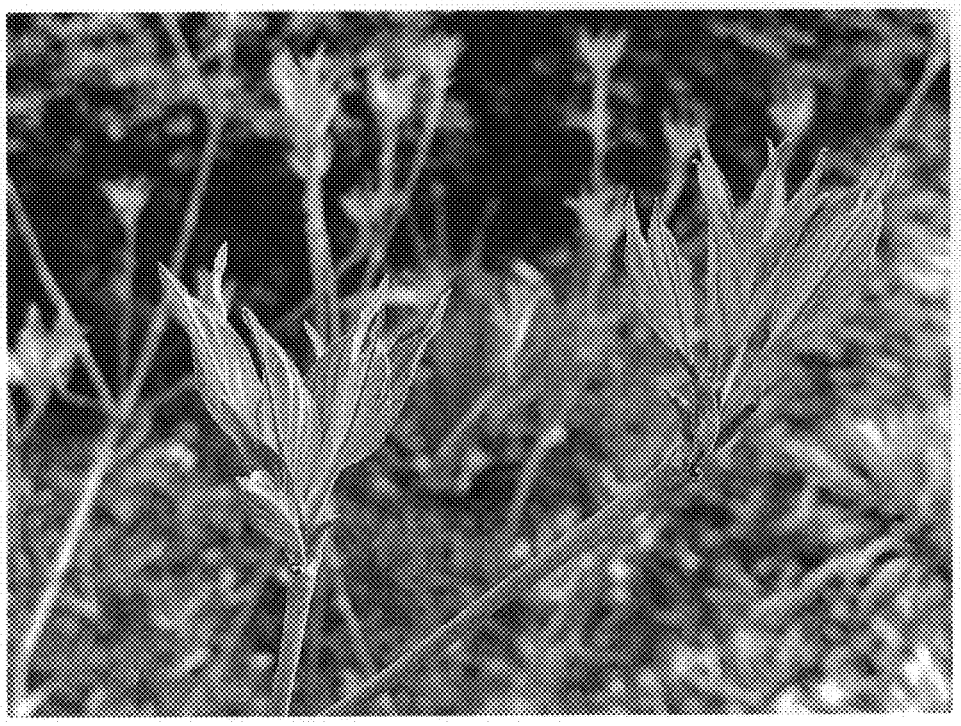
FIG. 3. Photograph of new leaf growth on 'Erica's Appalachian Sunrise'. Colors in the photograph may differ from actual colors due to lighting and light reflectance.
Figure 4:
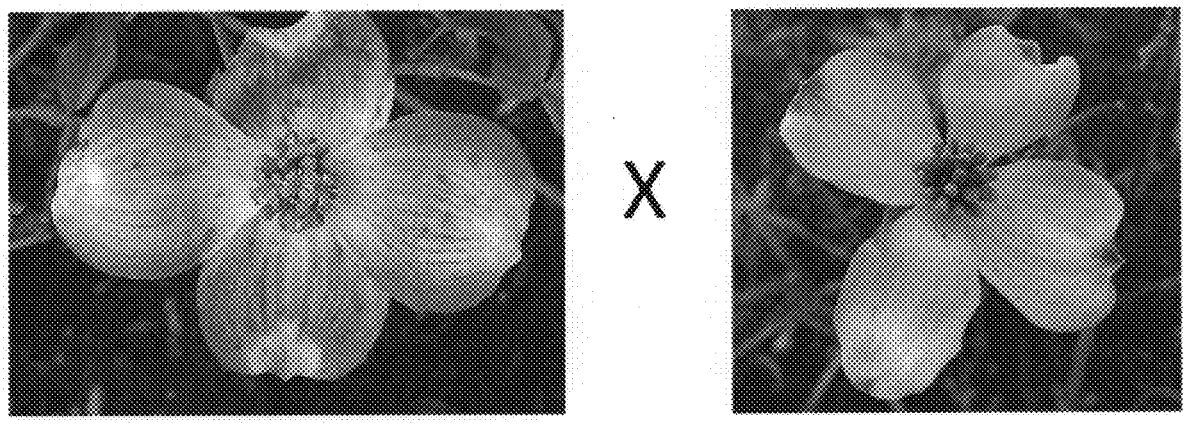
FIG. 4. Photographs of the bracts and flowers of dogwood cultivars 'Cherokee Brave' and 'Karen's Appalachian Blush', (U.S. Plant Pat. No. 13,165), which were initially crossed. Results show that the resulting F1 cultivar, 'Erica's Appalachian Sunrise', is not, as was expected, related to 'Karen's Appalachian Blush', but is the result of self-pollination of 'Cherokee Brave' (U.S. Plant Pat. No. 10,166). It can be seen that the lighter red or pink bracts of 'Erica's Appalachian Sunrise' (shown in FIG. 2) closely resemble the bracts of the parent, 'Cherokee Brave'.
Figure 5:
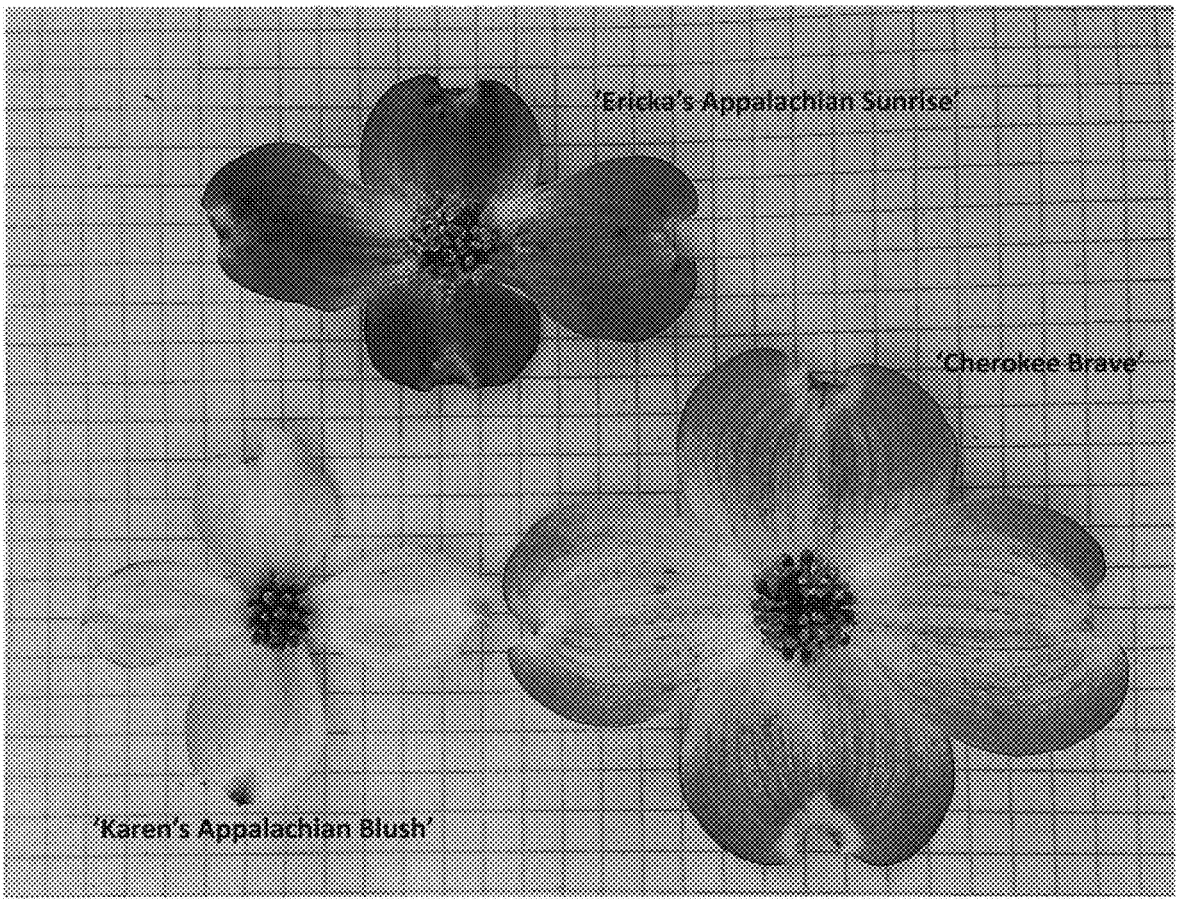
FIG. 5. Photograph of the less commonly produced bracts and flowers, less than about 5%, of the dogwood cultivar 'Erica's Appalachian Sunrise' (top—fully dark, red bracts), and those of 'Karen's Appalachian Blush' (bottom left) and 'Cherokee Brave' (bottom right).

A new and distinct cultivar of flowering dogwood tree producing both fully dark red bracts and lighter red or pink bracts. Both types of bracts are significantly smaller than the bracts of the parent cultivar, 'Cherokee Brave'. This dogwood tree cultivar is botanically known as *Cornus florida* and referred to by the following cultivar name: 'Erica's Appalachian Sunrise'. This cultivar appears to be highly resistant to powdery mildew caused by *Erisphe pulchra*.

This new and distinct dogwood tree cultivar is a product of self-pollination of the dogwood cultivar 'Cherokee Brave'. The subject dogwood tree cultivar differs from 'Cherokee Brave' in that the instant cultivar produces significantly smaller and both fully dark red bracts and lighter red bracts and also exhibits greater resistance to powdery mildew.

DETAILED BOTANICAL DESCRIPTION

The following observations, measurements and comparisons describe this cultivar grown in Maryville, Tenn. Trees used for this description were about ten (10) years old. Both the fully dark red bracts and lighter red to pink bracts are substantially the same size, though significantly smaller than the bracts produced by the parent cultivar. Plant hardiness is expected to be zones 4-9. The color characteristic descriptions use color references to The Royal Horticultural Society (R.H.S.) Colour Chart, The Royal Horticultural Society, London, UK, 4$^{th}$ Edition, 2001, except where general terms of ordinary dictionary significance are used.

A bee-mediated pollination between the dogwood cultivars 'Cherokee Brave' and 'Karen's Appalachian Blush' was conducted in April of 2009. Seeds were collected from both cultivars and planted in a greenhouse in Knoxville, Tenn. This new and distinct dogwood tree cultivar was discovered among the planting and germination of the seeds harvested from 'Cherokee Brave'. The following Table 1 shows the alleles at nine (9) loci compared between the cultivars 'Karen's Appalachian Blush' (U.S. Plant Pat. No. 13,165), 'Cherokee Brave', and the new cultivar 'Erica's Appalachian Sunrise'. As seen in Table 1, the alleles for 'Erica's Appalachian Sunrise' are identical at all nine (9) loci to those of 'Cherokee Brave' and have no alleles that match 'Karen's Appalachian Blush'. This demonstrates conclusively that dogwood cultivar 'Erica's Appalachian Sunrise' was the result of self-pollination of 'Cherokee Brave'. Asexual reproduction of 'Erica's Appalachian Sunrise' by grafting of axillary buds onto seedling rootstocks has shown that the unique features of this new dogwood cultivar are stable and reproduced true-to-type in successive vegetatively propagated generations.

TABLE 1

Allelic Comparisons at Nine (9) loci for dogwood cultivars 'Karen's Appalachian Blush' (KAB),'Cherokee Brave' (CB), and 'Erica's Appalachian Sunrise' (EAS)

| | | Loci/Primer | | | |
|---|---|---|---|---|---|
| Cultivar | CF213 | CF191 | CF273 | CF322 | CT585 |
| KAB (as base-pair size) | 270:270 | 132:169 | 140:144 | 137:173 | 167:187 |
| CB (as base-pair size) | 267:278 | 144:144 | 133:142 | 154:154 | 174:174 |
| EAS (F1) (as base-pair size) | 267:278 | 144:144 | 133:142 | 154:154 | 174:174 |

| | Loci/Primer | | | |
|---|---|---|---|---|
| Cultivar | CF597 | CF634 | CF713 | CF562 |
| KAB (as base-pair size) | 114:126 | 120:126 | 154:154 | 208:208 |
| CB (as base-pair size) | 105:120 | 113:113 | 144:144 | 212:225 |
| EAS (F1) (as base-pair size) | 105:120 | 113:113 | 144:144 | 212:225 |

TABLE 2

Simple Sequence Repeats and Associated Primers for Nine Loci shared by the Dogwood Cultivars 'Erica's Appalachian Sunrise' and 'Cherokee Brave'

| GenBank accession no. | Locus | Forward and Reverse Primer Sequences (5'-3') | Repeated Seq. |
|---|---|---|---|
| ED651856 | CF191 | F: AACCTGCATCTTCCCCAAGT (SEQ ID NO: 1) R: CCTTTTACCAACCCAACACG (SEQ ID NO: 2) | $(AG)_{20}$ $T(GA)_{12}$ $(GAA)_4$ |
| ED651874 | CF213 | F: TGCAAATGGTTATTGATTGCTCTC (SEQ ID NO: 3) R: ATTTGTTTCCCATGACCTGAAAGA (SEQ ID NO: 4) | $(CT)_9$ $(GT)_{12}$ |
| ED651920 | CF273 | F: TCATATTTATGCTTTCCTTGCCGT (SEQ ID NO: 5) R: GTGATCCTCTCCTAAGGACTTCCA (SEQ ID NO: 6) | $(AC)_{14}$ |
| ED651957 | CF322 | F: CTAACCTGCATCTTCCCCAAG (SEQ ID NO: 7) R: TTTACCAACCCAACACGACAC (SEQ ID NO: 8) | $(AG)_{20}$ $TG(AG)_{12}$ |
| ER870584 | CF562 | F: CCAGAGGTATGAATTCTGTGT (SEQ ID NO: 9) R: CTTGCAAATTGTTGTAATGAA (SEQ ID NO: 10) | $(GT)_{16}$ |
| ER870607 | CF585 | F: AACGAAGCAAGCAAAACAATC (SEQ ID NO: 11) R: ACCCCACCACTTCATCTCTC (SEQ ID NO: 12) | $(AT)_7$ $(GT)_{11}$ |
| ER870619 | CF597 | F: AAGTCAGATCATTTCAGATTAACA (SEQ ID NO: 13) R: CGAATTGACGATAAATACAAAATA (SEQ ID NO: 14) | $(AC)_{13}$ |
| ER870656 | CF634 | F: GAAATTCAAATTTTAAAGAAGTCC (SEQ ID NO: 15) R: TTGTATAGTACTTCAAGGCCACT (SEQ ID NO: 16) | $(AG)_{14}$ |
| ER870735 | CF713 | F: GATACTTATGCAATTAGGACACAA (SEQ ID NO: 17) R: GTAACAATGGTGGAAGGAAG (SEQ ID NO: 18) | $(TC)_{18}$ |

The cultivar 'Erica's Appalachian Sunrise' has some phenotypic similarities to the cultivar 'Cherokee Brave', but also distinct differences. The following Table 3 provides a comparison of those characteristics for each cultivar that have been observed. Measurements are provided as averages (with ranges also provided as indicated):

TABLE 3

Comparison of Characteristics for Three Dogwood Tree Cultivars

| | Character | 'Erica's Appalachian Sunrise' | 'Cherokee Brave' |
|---|---|---|---|
| 1 | Tree Height (observation) | 2 meters (at 8 years) | 2-3 meters (10-15 years) |
| 2 | Tree Form | Branching/ Spreading | Branching/ Spreading |
| 3 | Growth Rate | Slow 16 cm/year | Moderate 24 cm/year |
| 4 | Spread of Tree | 1.5 meters | 2.0 meters |
| 5 | Trunk Diam. at 1 meter | 6.5 cm | 8 cm |
| 6 | Trunk Texture | Smooth | Smooth |
| 7 | Primary Trunk Color/New Branches/ Texture | 144A New Growth Older Mature 201B/196B Smooth | 144A New Growth Older Mature 201B/196B Smooth |
| 8 | Presence of anthocyanin (observation) Coloration by anthocyanin on the immature leaf upper side | Red with Green Mainly 61B with some 143C | Red with Green Mainly 61B with some 143C |
| 9 | Color of mature leaf upper surface/ lower surface | Green 143C and some 61B More red than 'Cherokee Brave' and red is persistent through growing season/Green 143C | Green Group 136C, with very little red (mostly Green 136C for the growing season) |
| 10 | Color of leaves in autumn (observation) | Red-Purple 71A | Red-Purple 71A |
| 11 | Leaf shape | Ovate | Ovate |
| 12 | Leaf Margin | Entire | Entire |
| 13 | Leaf Tip | Cuspidate | Cuspidate |
| 14 | Leaf Base | Cuneate | Cuneate |
| 15 | Leaf Venation/ Texture | Palmate/Smooth with hairs | Palmate/Smooth with hairs |
| 16 | Leaf Length | 4.1-6.25 cm | 5.0-7.2 cm |
| 17 | Leaf Width | 0.8-1.2 cm | 1.0-2.0 cm |
| 18 | Petiole Length | <1 cm | <1 cm |
| 19 | Petiole Color | 134C | 134C |
| 20 | Petiole Texture | Smooth | Smooth |
| 21 | Flower diameter (measurement) | 6.5 mm open | 6.5 mm open |
| 22 | Floret color when open (observation) | Yellow Green 150A-150B with some purple 76A to 76B on top | Yellow Green 150A-150B with some purple 76A to 76B on top |
| 23 | Uniformity of bract size (observation) | See 24-29 | See 24-29 |
| 24 | Bract over-lapping (observation for both types) | Overlapping tips and edges | Slightly overlap |

TABLE 3-continued

Comparison of Characteristics for Three Dogwood Tree Cultivars

| | | | |
|---|---|---|---|
| 25 | Whole shape of bracts (observation) | Spade-shaped with point at the base | Tear-drop with blunt tip |
| 26 | Inner Bract length (measure-ment) | 23.1 mm (both types) | 38.8 mm |
| 27 | Inner Bract width (measure-ment) - modified cleft | 16.8 mm (both types) | 35.9 mm |
| 28 | Outer Bract width (measure) | 18.9 mm (both types) | 38.5 mm |
| 29 | Outer Bract length (measurement) | 15.3 mm (both types) | 30.3 mm |
| 30 | Number of bracts | 4 | 4 |
| 31 | Bract color (light red) | 63C - striated red-veined, on white (95%) | 63C - striated red-veined, on white, pure white base of bract |
| 32 | Bract color (dark red) | 182A to 181B (mostly solid color with some white striation near the base (<5%)) | 63C striated red-veined, on white, pure white base of bract |
| 33 | Cleft in Bract | Yellow Green 145C (<5%) | Some are almost pure white, others have same color as the bracts |
| 34 | Bract duration (both types) | Most bracts gone by mid-late April | Most bracts gone by mid-late April |
| 35 | Pedicel Length | 23.8 mm | 25.2 mm |
| 36 | Bract variegation (observation) | None | None |
| 37 | Pistil color (observation) | Yellow Green 150A-150B | Yellow Green 150A-150B |
| 38 | Fruit shape (observation) | Broadly oval | Broadly oval |
| 39 | Fruit length (measurement) | About 1.5 cm | About 1.5 cm |
| 40 | Fruit color (observation) | Red when mature in fall 45A to 45B | Red when mature in fall 45A to 45B |
| 41 | Fragrance (observation) | None | None |
| 42 | Flowering season (observation) | Spring | Spring |
| 43 | Flowering time (observation) | April | April |
| 44 | Deciduous or evergreen (observation) | Deciduous | Deciduous |
| 45 | Disease resistance (observation) | Highly resistant to powdery mildew caused by *Erisphe pulchra* but some Spot Anthracnose spotting by *Elsinoe cornii* | Moderately resistance to powdery mildew caused by *Erisphe pulchra* but some Spot Anthracnose by *Elsinoe cornii* |
| 46 | Bark color (mature) | 144A (mottled) | 144A (mottled) |
| 47 | Flower/ inflorescence number | 19.7 | 25.0 |
| 48 | Anther color | Purple 86A | Purple 86A |
| 49 | Flower petal length | 3-5 mm | 3-5 mm |

TABLE 3-continued

Comparison of Characteristics for Three Dogwood Tree Cultivars

| | | | |
|---|---|---|---|
| 50 | Flower petal color (closed) | Purple 76A to 76B on top and Yellow Green 150A-150B near bottom | Yellow Green group 149B (no purple) |
| 51 | Flower petal color (open) | 150A to 150B | 150A to 150B |

| | Character | 'Karen's Appalachian Blush' |
|---|---|---|
| 1 | Tree Height (observation) | 2-3 meters (10-15 years) |
| 2 | Tree Form | Narrow few branches |
| 3 | Growth Rate | Slow 12 cm/ year |
| 4 | Spread of Tree | 0.8 meters |
| 5 | Trunk Diam. at 1 meter | 5 cm |
| 6 | Trunk Texture | Smooth |
| 7 | Primary Trunk Color/New Branches/ Texture | 144C New Growth Older Mature 202A/196B Smooth |
| 8 | Presence of anthocyanin (observation) Coloration by anthocyanin on the immature leaf upper side | Green 143B |
| 9 | Color of mature leaf upper surface/ lower surface | 144C to 144B Both surfaces |
| 10 | Color of leaves in autumn (observation) | 71C to 71D |
| 11 | Leaf shape | Ovate |
| 12 | Leaf Margin | Entire |
| 13 | Leaf Tip | Cuspidate |
| 14 | Leaf Base | Cuneate |
| 15 | Leaf Venation/Texture | Palmate/Smooth with hairs |
| 16 | Leaf Length | 5.0-8.0 cm |
| 17 | Leaf Width | 2.0-2.5 cm |
| 18 | Petiole Length | 1.0-1.3 cm |
| 19 | Petiole Color | 149A |
| 20 | Petiole Texture | Smooth |
| 21 | Flower diameter (measurement) | 6.5 mm open |
| 22 | Floret color when open (observation) | Yellow Green 150A-150B with some purple 76A to 76B on top |
| 23 | Uniformity of bract size (observation) | See 24-29 |
| 24 | Bract overlapping (observation for both types) | Very little overlap |
| 25 | Whole shape of bracts (observation) | Linear |
| 26 | Inner Bract length (measurement) | 29.3 mm |
| 27 | Inner Bract width (measurement) - modified cleft | 20.4 mm |
| 28 | Outer Bract width (measure) | 23.8 mm |
| 29 | Outer Bract length (measurement) | 31.8 mm |
| 30 | Number of bracts | 4 |
| 31 | Bract color (light red) | White 155B |
| 32 | Bract color (dark red) | Some pink 49D around margins bleeding towards center |
| 33 | Cleft in Bract | Reduced and Violet purple 93B to Blush purple group N74C or creamy white with purple/red 84D |
| 34 | Bract duration (both types) | Most bract gone by mid-late April |
| 35 | Pedicel Length | 19.5 mm |
| 36 | Bract variegation (observation) | None |
| 37 | Pistil color (observation) | Yellow Green 150A-150B |
| 38 | Fruit shape (observation) | Broadly oval |
| 39 | Fruit length (measurement) | About 1.5 cm |
| 40 | Fruit color (observation) | Red when mature in fall 45A to 45B |
| 41 | Fragrance (observation) | None |
| 42 | Flowering season (observation) | Spring |
| 43 | Flowering time (observation) | April |
| 44 | Deciduous or evergreen (observation) | Deciduous |
| 45 | Disease resistance (observation) | Highly resistant to powdery mildew caused by *Erisphe pulchra* but some Spot Anthracnose *Elsinoe cornii* |
| 46 | Bark color (mature) | 144C |
| 47 | Flower/inflorescence number | 16.4 |
| 48 | Anther color | Purple 86A |
| 49 | Flower petal length | 3-5 mm |
| 50 | Flower petal color (closed) | Purple 76A to 76B on top and Yellow Green 150A-150B near bottom |
| 51 | Flower petal color (open) | 150C |

Botanical classification: *Cornus florida* 'Erica's Appalachian Sunrise'.

Unique features: A mixture of two types of bracts, a first one being less than about 5% of the bracts produced that is fully dark red and a second type being more than about 95% of the bracts produced that is similar in color to the bracts produced by the parent 'Cherokee Brave'. Both types of bracts on 'Erica's Appalachian Sunset' are similar in size and significantly smaller than the bracts produced by the parent 'Cherokee Brave'. Fewer flowers per inflorescence of 'Erica's Appalachian Sunset' than on 'Cherokee Brave'.

Disease susceptibility: 'Erica's Appalachian Sunrise' has a strong resistance to Powdery mildew caused by *Erisphe pulchra* and only some spotting caused by *Elsinoe corni*, a cosmetic disease with little damage.

Insect damage: None noted.

SEQUENCE LISTING

<160> NUMBER OF SEQ ID NOS: 18

<210> SEQ ID NO 1
<211> LENGTH: 20
<212> TYPE: DNA
<213> ORGANISM: Artificial Sequence
<220> FEATURE:
<223> OTHER INFORMATION: Forward primer sequence

<400> SEQUENCE: 1 aacctgcatc ttccccaagt 20

<210> SEQ ID NO 2
<211> LENGTH: 20
<212> TYPE: DNA
<213> ORGANISM: Artificial Sequence
<220> FEATURE:
<223> OTHER INFORMATION: Reverse primer sequence

<400> SEQUENCE: 2 ccttttacca acccaacacg 20

<210> SEQ ID NO 3
<211> LENGTH: 24
<212> TYPE: DNA
<213> ORGANISM: Artificial Sequence
<220> FEATURE:
<223> OTHER INFORMATION: Forward primer sequence

<400> SEQUENCE: 3 tgcaaatggt tattgattgc tctc 24

<210> SEQ ID NO 4
<211> LENGTH: 24
<212> TYPE: DNA
<213> ORGANISM: Artificial Sequence
<220> FEATURE:
<223> OTHER INFORMATION: Reverse primer sequence

<400> SEQUENCE: 4 atttgtttcc catgacctga aaga 24

<210> SEQ ID NO 5
<211> LENGTH: 24
<212> TYPE: DNA
<213> ORGANISM: Artificial Sequence
<220> FEATURE:
<223> OTHER INFORMATION: Forward primer sequence

<400> SEQUENCE: 5 tcatatttat gctttccttg ccgt 24

<210> SEQ ID NO 6
<211> LENGTH: 24
<212> TYPE: DNA
<213> ORGANISM: Artificial Sequence
<220> FEATURE:
<223> OTHER INFORMATION: Reverse primer sequence

<400> SEQUENCE: 6 gtgatcctct cctaaggact tcca 24

<210> SEQ ID NO 7
<211> LENGTH: 21

-continued

<212> TYPE: DNA
<213> ORGANISM: Artificial Sequence
<220> FEATURE:
<223> OTHER INFORMATION: Forward primer sequence

<400> SEQUENCE: 7 ctaacctgca tcttccccaa g 21

<210> SEQ ID NO 8
<211> LENGTH: 21
<212> TYPE: DNA
<213> ORGANISM: Artificial Sequence
<220> FEATURE:
<223> OTHER INFORMATION: Reverse primer sequence

<400> SEQUENCE: 8 tttaccaacc caacacgaca c 21

<210> SEQ ID NO 9
<211> LENGTH: 21
<212> TYPE: DNA
<213> ORGANISM: Artificial Sequence
<220> FEATURE:
<223> OTHER INFORMATION: Forward primer sequence

<400> SEQUENCE: 9 ccagaggtat gaattctgtg t 21

<210> SEQ ID NO 10
<211> LENGTH: 21
<212> TYPE: DNA
<213> ORGANISM: Artificial Sequence
<220> FEATURE:
<223> OTHER INFORMATION: Reverse primer sequence

<400> SEQUENCE: 10 cttgcaaatt gttgtaatga a 21

<210> SEQ ID NO 11
<211> LENGTH: 21
<212> TYPE: DNA
<213> ORGANISM: Artificial Sequence
<220> FEATURE:
<223> OTHER INFORMATION: Forward primer sequence

<400> SEQUENCE: 11 aacgaagcaa gcaaaacaat c 21

<210> SEQ ID NO 12
<211> LENGTH: 20
<212> TYPE: DNA
<213> ORGANISM: Artificial Sequence
<220> FEATURE:
<223> OTHER INFORMATION: Reverse primer sequence

<400> SEQUENCE: 12 accccaccac ttcatctctc 20

<210> SEQ ID NO 13
<211> LENGTH: 24
<212> TYPE: DNA
<213> ORGANISM: Artificial Sequence
<220> FEATURE:
<223> OTHER INFORMATION: Forward primer sequence

<400> SEQUENCE: 13

-continued

```
aagtcagatc atttcagatt aaca                                          24


<210> SEQ ID NO 14
<211> LENGTH: 24
<212> TYPE: DNA
<213> ORGANISM: Artificial Sequence
<220> FEATURE:
<223> OTHER INFORMATION: Reverse primer sequence

<400> SEQUENCE: 14

cgaattgacg ataaatacaa aata                                          24


<210> SEQ ID NO 15
<211> LENGTH: 24
<212> TYPE: DNA
<213> ORGANISM: Artificial Sequence
<220> FEATURE:
<223> OTHER INFORMATION: Forward primer sequence

<400> SEQUENCE: 15

gaaattcaaa ttttaaagaa gtcc                                          24


<210> SEQ ID NO 16
<211> LENGTH: 23
<212> TYPE: DNA
<213> ORGANISM: Artificial Sequence
<220> FEATURE:
<223> OTHER INFORMATION: Reverse primer sequence

<400> SEQUENCE: 16

ttgtatagta cttcaaggcc act                                           23


<210> SEQ ID NO 17
<211> LENGTH: 24
<212> TYPE: DNA
<213> ORGANISM: Artificial Sequence
<220> FEATURE:
<223> OTHER INFORMATION: Forward primer sequence

<400> SEQUENCE: 17

gatacttatg caattaggac acaa                                          24


<210> SEQ ID NO 18
<211> LENGTH: 20
<212> TYPE: DNA
<213> ORGANISM: Artificial Sequence
<220> FEATURE:
<223> OTHER INFORMATION: Reverse primer sequence

<400> SEQUENCE: 18

gtaacaatgg tggaaggaag                                               20
```

We claim:

1. A new and distinct cultivar of Dogwood tree, *Cornus florida*, named 'ERICA'S APPALACHIAN SUNRISE', as illustrated and described.

* * * * *

'Cherokee Brave' 'Appalachian Blush'